(12) United States Patent
Hartley et al.

(10) Patent No.: US 7,867,270 B2
(45) Date of Patent: Jan. 11, 2011

(54) MULTI-PORT DELIVERY DEVICE

(75) Inventors: David Ernest Hartley, Subiaco (AU); Krasnodar Ivancev, Lund (SE); Michael Lawrence-Brown, City Beach (AU)

(73) Assignees: William A. Cook Australia Pty. Ltd., Queensland (AU); Cook Incorporated, Bloomington (IN); William Cook Europe ApS, Bjaeverskov (DK)

( * ) Notice: Subject to any disclaimer, the term of this patent is extended or adjusted under 35 U.S.C. 154(b) by 686 days.

(21) Appl. No.: 11/807,878

(22) Filed: May 30, 2007

(65) Prior Publication Data
US 2007/0299499 A1    Dec. 27, 2007

Related U.S. Application Data

(60) Provisional application No. 60/810,316, filed on Jun. 2, 2006.

(51) Int. Cl.
A61F 2/06  (2006.01)
(52) U.S. Cl. ..................................... 623/1.11
(58) Field of Classification Search ............... 623/1.13, 623/1.15, 1.23–1.25; 606/191–198
See application file for complete search history.

(56) References Cited

U.S. PATENT DOCUMENTS 6,350,278 B1 * 2/2002 Lenker et al. .............. 623/1.12

2004/0230287 A1 * 11/2004 Hartley et al. .............. 623/1.12

FOREIGN PATENT DOCUMENTS

| WO | WO01/67993 A2 | 9/2001 |
| WO | WO03/101518 A1 | 12/2003 |
| WO | WO2004/089249 A1 | 10/2004 |
| WO | PCT/US2007/012730 | 11/2007 |

OTHER PUBLICATIONS

International Search Report/PCT/US2007/012730, Nov. 28, 2007, EPO.

* cited by examiner

Primary Examiner—Kevin T Truong
(74) Attorney, Agent, or Firm—Richard J. Godlewski

(57) ABSTRACT

A multi-port stent graft delivery device (2) has an annular access lumen (26) between a delivery catheter (24) and a main sheath (6), at least one indwelling access sheath (28, 30) within the access lumen, and an indwelling guide wire (36, 38) within the or each access sheath and a stent graft (16) retained in the delivery device. Upon deployment of the stent graft into the vasculature of a patient the indwelling guide wire can be used to facilitate stabilization of the access sheath during cathertization of a side branch and deployment of a side arm covered or uncovered stent therein through the advanced access sheath. A manifold associated (4) with a handle provides a plurality of access ports (41, 43). A docking balloon may also be used.

21 Claims, 8 Drawing Sheets

MULTI-PORT DELIVERY DEVICE

CROSS-REFERENCE TO RELATED APPLICATIONS

This application claims priority of provisional application Ser. No. 60/810,316, filed Jun. 2, 2006.

TECHNICAL FIELD

This invention relates to a medical device and more particularly to a device for introduction of stent grafts into the vasculature of a patient.

BACKGROUND OF THE INVENTION

It is known to introduce endovascular stent grafts into the vasculature of a patient to bridge an aneurism or damaged portion of the wall of the vasculature. Problems can occur however, where the damage to the vasculature includes or is adjacent to a branch vessel from a main artery because occlusion of the branch vessel may cause permanent damage to the patient.

Examples of such branch vessels are the renal and the mesenteric arteries extending from the aorta.

Fenestrations in a stent graft have been proposed to allow access to the branch vessel from a main stent graft but it is often necessary to provide a side branch graft to maintain access into the branch vessel.

A problem exists, however, with the catheterisation of such a branch vessel to enable deployment of a covered stent or uncovered stent into the side vessel and it is the object of this invention to provide a method to facilitate catheterisation. The problem can be exacerbated in the region of the renal arteries where there are normally two renal arteries substantially adjacent to each other extending from the aorta and is necessary to have two arrangements for catheterisation within the stent graft.

Normally a stent graft introducer device would include a pusher catheter but where catheterisation devices for the branch vessels are to also be included there is not enough room within the containing sheath for a stent graft introducer having regard to the diameter of the vasculature through which it must be introduced to include a full pusher catheter.

The overall diameter of the delivery device is restricted by the diameter of the vessels through which access is to be obtained. The usual route to access the aorta using the Seldinger technique is via the femoral and iliac arteries and this restricts the diameter of a delivery device to about 24 French (7.6 mm diameter).

These arrangements have therefore required a considerable redesign of the delivery device and it is to that redesign that the present invention is directed.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form, therefore, the invention is said to reside in a multi-port stent graft delivery device comprising;

a guide wire catheter having a guide wire lumen therethrough;

a handle at a distal end of the guide wire catheter, the handle including a plurality of access ports;

a nose cone dilator at the proximal end of the guide wire catheter;

a sheath arrangement extending from the handle to the nose cone dilator, the sheath arrangement being coaxial with and surrounding the guide wire catheter and defining an annular access lumen between the guide wire catheter and the sheath arrangement;

a stent graft on the guide wire catheter and within the main sheath, the stent graft comprising a proximal end, a distal end, a peripheral wall defining a lumen therethrough and at least one fenestration in the peripheral wall;

the proximal end of the stent graft being releasably retained by a retention and release arrangement distally of the nose cone dilator;

at least one indwelling access sheath within the access lumen, the at least one indwelling access sheath extending from the handle and having a proximal end terminating distally of the stent graft;

an indwelling guide wire within the or each access sheath;

the indwelling guide wire extending through the stent graft and exiting the at least one fenestration and extending proximally within the main sheath;

whereby upon deployment of the stent graft into the vasculature of a patient the indwelling guide wire can be used to facilitate cathertisation of a side branch or target vessel or be used to stabilise the access sheath during catheterisation, advancement of the access sheath into the target vessel and deployment of a covered or uncovered stent therein through the access sheath.

Preferably there is a dilator extending through the or each access sheath and comprising a dilator tip at the proximal end of the or each access sheaths, the dilator being able to be withdrawn through the access sheath.

In one embodiment the retention and release arrangement distal of the nose cone dilator for the proximal end of the stent graft comprises a distally facing capsule fixed to the nose cone dilator and the proximal end of the stent graft is received in the capsule. The stent graft can comprise a proximal exposed stent and the proximal exposed stent can be received in the capsule and the stent graft can be released by advancement of the nose cone dilator.

In an alternative embodiment the retention and release arrangement distal of the nose cone dilator for the proximal end of the stent graft comprises a trigger wire system engaging the stent graft or a stent of the stent graft. The stent graft can comprise a proximal exposed stent and the proximal exposed stent can be engaged by the trigger wire system.

Preferably the stent graft includes diameter reducing ties and the delivery device further includes a release arrangement on the handle for the diameter reducing ties.

The release arrangement for the diameter reducing ties can comprise a first release grip on the handle and a release wire extending from the first release grip to the diameter reducing ties.

After removal of the dilator a catheter may be advanced through the or each access sheath. The catheter can be formed from a flexible material and can comprise a preformed curve at its proximal end.

There may be further included a retention arrangement for the distal end of the stent graft comprising a tie arrangement engaging the stent graft, a second release grip on the handle and at least one trigger wire extending from the second release grip to the tie arrangement.

The guide wire catheter may include a sleeve to act as a guide for the trigger wires. The sleeve may extend from the handle and terminate just distal of the stent graft retained onto the guide wire catheter. A similar sleeve can be attached to the nose cone dilator and extend distally from the nose cone dilator to act as an engagement point for the trigger wires for the exposed stent. The sleeve can also act as the mounting point for the tie arrangement for the distal end of the stent graft.

The sheath arrangement may comprise an inner sheath extending proximally from the handle and a outer sheath including a sheath retractor on the inner sheath to withdraw the outer sheath to expose the stent graft.

The handle can comprise a haemostatic seal assembly and the delivery catheter and the or each access sheath extends through the haemostatic seal assembly.

The haemostatic seal assembly can comprise a silicone disc assembly and the delivery catheter and the or each indwelling access sheath extend through respective apertures in the silicone disc assembly.

Alternatively the handle assembly can comprise a bifurcated or trifurcated tube assembly comprising two or three arms extending from a main tube and a haemostatic seal and access port on each of the arms and a respective one of the delivery catheter and the or each indwelling access sheath extending through a respective tube and haemostatic seal and access port.

Alternatively the handle can comprise a manifold assembly having a manifold body with a single aperture an one end and three or four spaced apart access ports at another end and a haemostatic seal on each of the spaced access ports and a respective one of the delivery catheter and the or each indwelling access sheath extending through a respective access port and haemostatic seal.

The fenestration or fenestrations in the stent graft can comprise a hinged fenestration having an enlarged aperture in the peripheral wall of the stent graft and a smaller fenestration within the enlarged aperture and a frusto-conical cone of graft material between the enlarged aperture and the smaller aperture. The enlarged aperture and the smaller aperture can each have a resilient ring peripheral reinforcement. The resilient ring peripheral reinforcement of the enlarged aperture and the smaller aperture may be connected by a hinge arrangement and the hinge arrangement between the enlarged aperture and the smaller aperture can be an integral hinge. The resilient ring peripheral reinforcement of the enlarged aperture and the smaller aperture can comprise a continuous length of a resilient shape memory wire.

The indwelling guide wire extending through the stent graft and exiting the at least one fenestration and extending proximally within the main sheath may be releasably fastened to the peripheral wall of the stent graft proximally of the fenestration to stabilise the indwelling guide wire during advancement of the dilator and access sheath and catheterisation of the branch vessel.

The releasable fastening may comprise a release wire stitched in to peripheral wall of the stent graft proximally of the fenestration, an engagement protrusion of the indwelling guide wire and a suture engaged around the release wire and the indwelling guide wire distally of the engagement protrusion whereby upon retraction of the release wire the suture is released from engagement with the indwelling guide wire.

In an alternative form the invention is said to reside in a stent graft delivery device comprising;

a guide wire catheter having a guide wire lumen therethrough;

a handle at a distal end of the guide wire catheter;

a nose cone dilator at the proximal end of the guide wire catheter, the nose cone dilator having a distally opening capsule thereon;

a sheath arrangement comprising an inner sheath extending proximally from the handle and a outer sheath including a sheath retractor on the inner sheath and extending to the nose cone dilator to withdraw the outer sheath, the sheath arrangement being coaxial with and surrounding the guide wire catheter and defining an annular access lumen between the guide wire catheter and the sheath arrangement;

a stent graft on the guide wire catheter and within the main sheath, the stent graft having a peripheral wall defining a lumen therethrough and at least one fenestration in the peripheral wall;

the stent graft having a proximally extending exposed stent and the exposed stent being releasably retained in the capsule of the nose cone dilator;

at least one indwelling access sheath within the access lumen, the at least one indwelling access sheath extending from the handle and having a proximal end terminating distally of the stent graft;

an indwelling guide wire within the or each access sheath;

the indwelling guide wire extending through the stent graft and exiting the fenestration and extending proximally within the main sheath and being received in the capsule of the nose cone dilator;

whereby upon deployment of the stent graft into the vasculature of a patient the indwelling guide wire can be used to facilitate catherisation of a side branch or target vessel or be used to stabilise the access sheath during catheterisation, advancement of the access sheath into the target vessel and deployment of a covered or uncovered stent therein through the access sheath.

There may be further included a docking balloon arrangement comprising a balloon guide extending into the capsule and affixed therein whereby upon completion of deployment of the stent graft, a balloon catheter including an inflatable balloon thereon can be advanced over the balloon guide at least partially into the capsule whereby the balloon can be inflated therein to provide a smooth transition from the nose cone to a delivery catheter for retraction of the nose cone dilator through the deployed stent graft.

In an alternative form the invention comprises in a multi-port stent graft delivery device comprising;

a guide wire catheter having a guide wire lumen therethrough;

a handle at a distal end of the guide wire catheter, the handle comprising a manifold assembly having a manifold body with a single aperture at a proximal end and three spaced apart access ports at a distal end and a haemostatic seal on each of the spaced apart access ports;

a nose cone dilator at the proximal end of the guide wire catheter, the nose cone dilator having a distally opening capsule thereon;

a sheath arrangement comprising an inner sheath extending proximally from the handle and a outer sheath including a sheath retractor on the inner sheath and extending to the nose cone dilator to withdraw the outer sheath, the sheath arrangement being coaxial with and surrounding the guide wire catheter and defining an annular access lumen between the guide wire catheter and the sheath arrangement;

a stent graft on the guide wire catheter and within the main sheath, the stent graft having a tubular peripheral wall defining a lumen therethrough and at least one fenestration in the peripheral wall;

the stent graft having a proximally extending exposed stent and the exposed stent being releasably retained in the capsule of the nose cone dilator;

two access sheaths within the access lumen, the access sheaths extending from one of the spaced apart access ports in the manifold assembly and through the access lumen proximally and having a proximal end terminating distally of the stent graft;

a dilator and indwelling guide wire within the or each access sheath;

the indwelling guide wire extending through the stent graft and exiting the fenestration and extending proximally within the main sheath and being received in the capsule of the nose cone dilator;

a respective one of the delivery catheter and the or each indwelling access sheath extending through a respective access port and haemostatic seal;

a docking balloon arrangement comprising a balloon guide extending from one of the spaced apart access ports in the manifold assembly and through the access lumen proximally into the capsule and affixed therein;

whereby upon deployment of the stent graft into the vasculature of a patient the indwelling guide wire can be used to facilitate cathertisation of a side branch or target vessel or be used to stabilise the access sheath during catheterisation, advancement of the access sheath into the target vessel and deployment of a covered or uncovered stent therein through the access sheath.

The balloon guide can include a balloon catheter whereby upon completion of deployment of the stent graft, the balloon catheter including an inflatable balloon thereon can be advanced through the access port over the balloon guide at least partially into the capsule whereby the balloon can be inflated therein to provide a smooth transition from the nose cone to a delivery catheter for retraction of the nose cone dilator through the deployed stent graft.

Alternatively the balloon catheter may be resident into the deployment device and the balloon catheter can be advanced into the capsule as discussed above upon completion of deployment of the stent graft.

The indwelling guide wire extending through the stent graft and exiting the at least one fenestration and extending proximally within the main sheath may be releasably fastened to the peripheral wall of the stent graft proximally of the fenestration to stabilise the indwelling guide wire during advancement of the dilator and access sheath and catheterisation of the branch vessel.

The releasable fastening may comprise a release wire stitched in to peripheral wall of the stent graft proximally of the fenestration, an engagement protrusion of the indwelling guide wire and a suture engaged around the release wire and the indwelling guide wire distally of the engagement protrusion whereby upon retraction of the release wire the suture is released from engagement with the indwelling guide wire.

It will be seen that by the various embodiments of the invention there is provided a device where the main delivery catheter and the sheaths for each of the side branch catheterisation devices are included within the main sheath of the stent graft with each of the components being able to be manipulated separately.

This then generally describes the invention but to assist with understanding reference will now be made the accompanying drawings which show preferred embodiments of the invention.

BRIEF DESCRIPTION OF THE DRAWING

In the drawings:

FIG. 2A shows stylised detail of the proximal end of an alternative embodiment of stent graft introducer including a fenestrated stent graft;

FIG. 2B shows detail of an arrangement to retain a guide wire to a proximal end of a stent graft;

FIG. 2C shows detail of a hinged fenestration as one embodiment of a fenestration for the proximal end of a stent graft;

DETAILED DESCRIPTION

Figure 1:
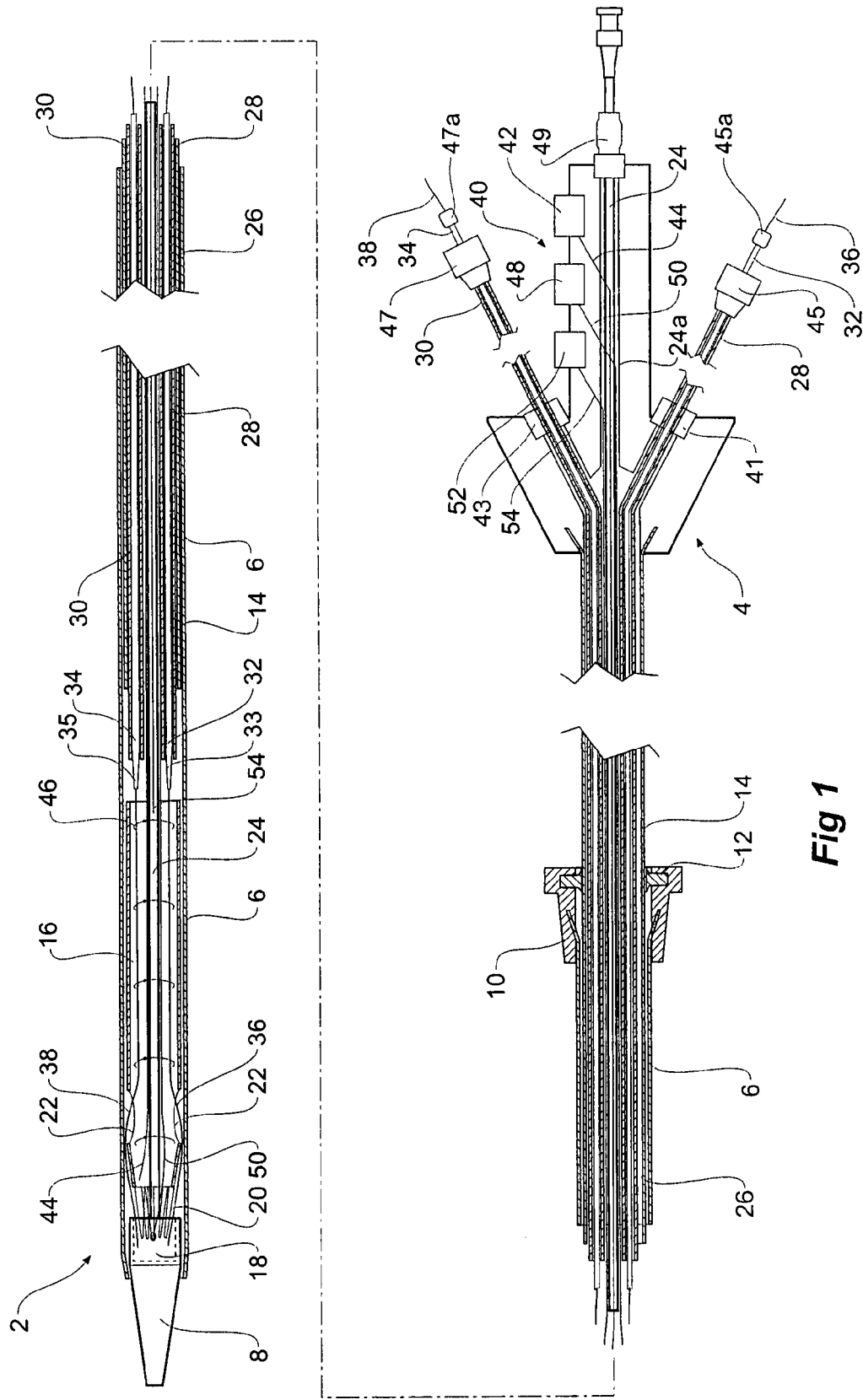
FIG. 1 shows a stylised version of a first embodiment of stent graft introducer according to the present invention.

FIG. 1 shows in a stylised manner a first embodiment of stent graft introducer according to the present invention. In this embodiment the introducer 2 comprises a handle arrangement 4, an inner sheath 14 extending proximally from the handle arrangement with an outer sheath 6 on the inner sheath 14 and extending forward to a nose cone dilator 8 at the proximal end of the device. In use the handle is intended to remain outside a patient and the outer sheath and nose cone dilator are intended to be introduced into a patient. The outer sheath 6 is mounted onto a sheath manipulator 10 which includes a hemostatic seal 12 which engages and seals onto the inner sheath 14. The sheath manipulator 10 is mounted proximally of the handle 4 such that movement of the sheath manipulator 10 towards the handle 4 on the inner sheath 14 withdraws the sheath 6 from a stent graft 16 retained distally of the nose cone dilator 8.

The nose cone dilator 8 has a distally facing capsule 18 at its distal end and struts of an exposed stent 20 of the stent graft 16 are received in the capsule to retain the stent graft therein.

The stent graft includes fenestrations 22. A guide wire catheter 24 extends from the handle 4 to and through the nose cone dilator 8. The guide wire catheter 24 extends within the annular space 26 within the sheath 6. The guide wire catheter passes through a guide wire lumen 24*a* in the handle.

Also within the annular space 26 and extending through and from the handle 4 are first and second access sheaths 28 and 30. The access sheaths 28 and 30 terminate just distal of the stent graft 16 within the sheath. Within the access sheaths 28 and 30 are dilators 32 and 34 respectively which extend proximally to dilator tips 35 and 33 respectively at the proximal ends of the access sheaths. Within the dilators 32 and 34 are indwelling guide wires 36 and 38 respectively. The indwelling guide wires extend from the handle through the dilators to the dilator tips and into the stent graft 16 and pass out to the fenestrations 22 and extend proximally and are received within the capsule 18 of the nose cone dilator 8.

The access sheaths 28 and 30 exit distally out of the handle 4 via haemostatic seals 41 and 43 respectively. The dilators 32 and 34 exit out of the distal end of the access sheaths 28 and 30 via haemostatic seals 45 and 47 respectively. The indwelling guide wires 36, 38 exit the dilators 32, 34 respectively haemostatic seals 45a and 47a respectively. A pin vice 49 is provided on the back of the handle for the guide wire catheter 24 to prevent movement of the guide wire catheter with respect to the handle when tightened and to allow relative movement when loosened.

The handle 4 includes trigger wire release mechanisms 40 for three retention arrangements associated with the stent graft.

A first trigger wire release 42 includes a trigger wire 44 which extends to diameter reducing ties 46 which hold the stent graft in a partially retracted state after the sheath 6 has been removed from it. A second trigger wire release 48 has a trigger wire 50 which extends to the top cap 18 and prevents removal of the struts 20 of the exposed stent of the stent graft until it has been removed.

A third trigger wire release 52 has a trigger wire 54 which extends to a distal retention for the stent graft 16 to the guide wire catheter 24.

In use the introducer is deployed into the vasculature of a patient and correctly oriented by the use of radiopaque markers on the stent graft (not shown). The outer sheath 6 can then be withdrawn by retracting the sheath manipulator 10 over the inner sheath 14. The indwelling guide wires 36 and 38 can then be withdrawn from the nose cone dilator and used to access the side vessels of the vasculature. For this purpose the dilators and access sheaths can be advanced such that the dilator tips extend through the fenestrations and the proximal end of the access sheaths are at the fenestrations. Subsequently the dilators can be withdrawn. The indwelling guide wires act as stabilisers for the access sheaths and separate guide wires advanced through the access sheaths or itself can be used for accessing the side vessels.

Alternatively the dilators and access sheaths can be advanced such that the dilator tips extend through the fenestrations and the proximal end of the access sheaths are at the fenestrations. Subsequently the dilators can be withdrawn and a further guide wire can then be advanced through the access sheath and an indwelling catheter 32 and 34 which may include a resilient tip in the shape of a hockey stick tip or crook can be used to assist in directing the guide wire transversally to access a branch vessel. The indwelling catheter can then be advanced into the vasculature and a suitable covered stent deployed through the access sheaths to provide a bridge between the main stent graft and the side vessels after the stent graft has been released from the delivery device.

Figure 2:
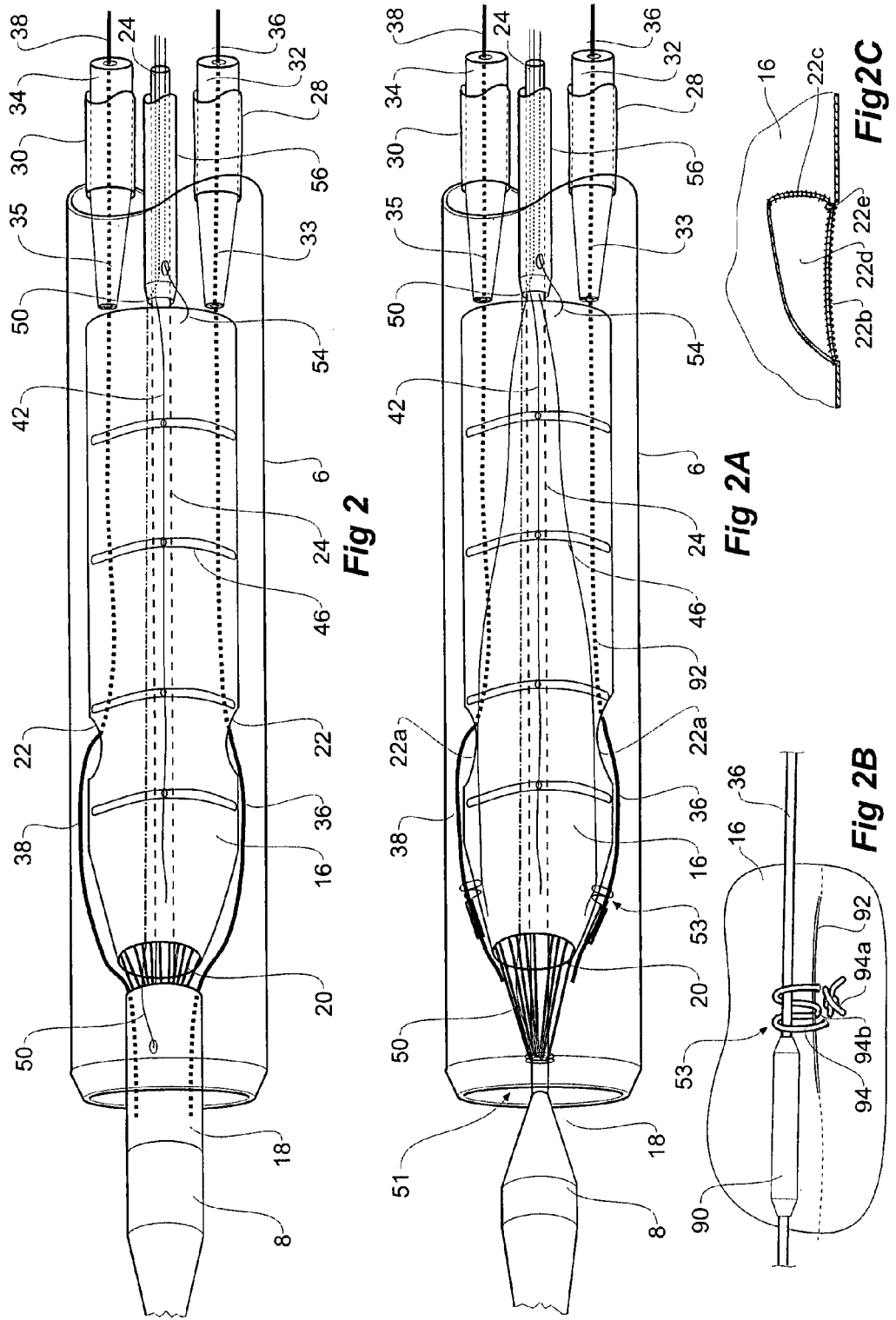
FIG. 2 shows stylised detail of the proximal end of a stent graft introducer including a fenestrated stent graft.

FIG. 2 shows more detail of the proximal end of the deployment device with a stent graft retained in it in a stylised form. In this illustration the same reference in numerals will be used for corresponding items as in FIG. 1.

It will be seen that the main guide wire catheter 24 extends to the nose cone dilator 8. Around the main guide wire catheter 24 is a sleeve 56. This sleeve provides an annular lumen between the sleeve and the main guide wire catheter 24 through which the trigger wires 42, 50 and 54 extend back to the handle and the trigger wire release mechanisms as shown in FIG. 1. The sheath 6 is shown larger than it would normally be. It would normally have a diameter to just fit over the capsule 18 and to retain the stent graft in a compressed condition. Indwelling access sheaths 28 and 30 terminate distally of the stent graft 16 and dilators 32 and 34 extend through the access sheaths and terminate in dilator tips 35 and 33.

The stent graft 16 has fenestrations 22 toward its proximal end.

The dilator tips 35 and 33 are positioned at the proximal ends of the access sheaths and distal of the distal end of the stent graft during introduction of the stent graft introducer and are advanced through the stent graft to the fenestrations after the main sheath is withdrawn as discussed below. The dilators can be withdrawn through the access sheaths after the access sheaths have been advanced to the fenestrations of the stent graft. The dilator are useful to prevent fouling of the access sheaths with stents of the stent graft during advancement of the access sheaths.

Indwelling guide wires 36 and 38 extend through the dilators, proximally to the fenestrations 22 in the stent graft 16, exit the stent graft at the fenestrations and extend into the capsule 18 of the nose cone dilator 8 to be retained therein during delivery.

Diameter reducing ties 46 on the stent graft 16 are retained by means of trigger wire 42. The diameter reducing ties hold the stent graft in a semi-expanded position after the sheath has been withdrawn during deployment. This enables some manipulation of the stent graft by movement of the main guide wire catheter while the exposed stent at the proximal end is retained within the capsule by trigger wire 50 and the distal end is retained to the guide wire catheter or the sleeve 56 by trigger wire 54.

FIG. 2A shows more detail of an alternative embodiment of the proximal end of the deployment device with a stent graft retained in it in a stylised form. In this illustration the same reference in numerals will be used for corresponding items as in FIG. 2. In this embodiment the nose cone dilator does not have a distally opening capsule and the proximal exposed stent 20 of the stent graft 16 is retained to the guide wire catheter by a trigger wire and suture arrangement 51. Retention is by fastening struts of the proximal exposed stent to a trigger wire catheter (not shown) by means of a sutures as is explained in PCT Patent Publication WO 03/101518 entitled "Trigger Wire System for a Prosthesis Deployment Device" the teaching of which is incorporated herein in its entirety.

It will be seen that the main guide wire catheter 24 extends to the nose cone dilator 8. Around the main guide wire catheter 24 is a sleeve 56. This sleeve provides an annular lumen between the sleeve and the main guide wire catheter 24 through which trigger wires extend back to the handle and the trigger wire release mechanisms as shown in FIG. 1. The sheath 6 is shown larger than it would normally be. It would normally have a diameter to just fit over the capsule 18. Indwelling access sheaths 28 and 30 terminate distally of the stent graft 16 and dilators 32 and 34 extend through the access sheaths and terminate in dilator tips 35 and 33.

The stent graft 16 has fenestrations 22a toward its proximal end. In this embodiment the fenestrations comprise hinged fenestrations and are shown in more detail in FIG. 2C.

The dilator tips 35 and 33 are positioned at the proximal ends of the access sheaths and distal of the distal end of the stent graft during introduction of the stent graft introducer and are advanced through the stent graft to the fenestrations after the main sheath is withdrawn as discussed below. The dilators can be withdrawn through the access sheaths after the access sheaths have been advanced to the fenestrations of the stent graft. The dilator are useful to prevent fouling of the access sheaths with stents of the stent graft during advancement of the access sheaths.

Indwelling guide wires 36 and 38 extend through the dilators, proximally to the fenestrations 22a, exit the stent graft at the fenestrations and extend proximally. To stabilise the guide wires proximally of the fenestrations during delivery a retention system 53 can be used. The retention system is shown in detail in FIG. 2B.

Diameter reducing ties 46 are retained by means of trigger wire 42. The diameter reducing ties hold the stent graft in a semi-expanded position after the sheath has been withdrawn during deployment. This enables some manipulation of the stent graft by movement of the main guide wire catheter while the exposed stent at the proximal end is retained by suture arrangement 51 and the distal end is retained to the guide wire catheter or the sleeve 56 by trigger wire 54.

FIG. 2B shows detail of the retention system 53 by which the guide wire 36 is stabilised proximally of the fenestration.

The guide wire 36 has a protrusion 90 soldered or crimped onto the guide wire and a suture 94 is fastened around the guide wire distally of the protrusion 94 and around a release wire 92 which is stitched through the stent graft 16 and then the suture 94 is sewn at 94a into the graft 16. When the release wire 92 is retracted the loop 94b of the suture 94 is released and the guide wire 36 can be retracted.

Although the retention system 53 is illustrated as being used with the delivery device without a capsule as shown in FIG. 2A the retention system shown in FIG. 2B can also be advantageously used with the delivery device shown in FIG. 2.

FIG. 2C shows detail in longitudinal cross section of the hinged fenestration 22a shown in FIG. 2A.

The fenestrations 22a comprise hinged fenestrations have an enlarged aperture 22b in the peripheral wall of the stent graft 16 and a smaller fenestration 22c within the enlarged aperture and a frusto-conical cone of graft material 22d between the enlarged aperture 22b and the smaller aperture 22c. The enlarged aperture and the smaller aperture each have a resilient ring peripheral reinforcement. The resilient ring peripheral reinforcement of the enlarged aperture and the smaller aperture are be connected by an integral hinge arrangement 22e. The resilient ring peripheral reinforcement of the enlarged aperture and the smaller aperture can comprise a continuous length of a resilient shape memory wire.

Figure 3:
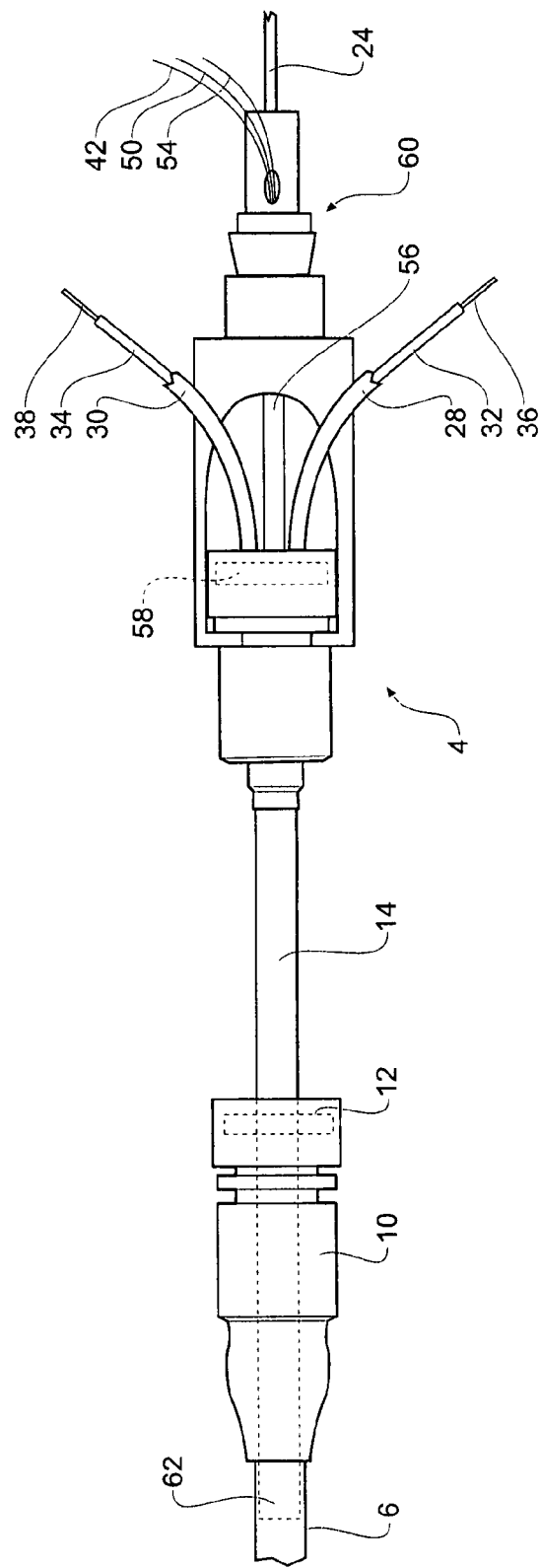
FIG. 3 shows one embodiment of the distal end of a stent graft introducer according the present invention.

FIG. 3 shows one embodiment of the distal or handle end of a stent graft introducer according to the present invention.

In FIG. 3 the same reference numerals are used for corresponding items to those shown in FIG. 1.

In this embodiment the handle 4 includes a manifold and hemostatic seal 58 through which pass the access sheaths 28 and 30 and the guide wire catheter 24 and sleeve 56. The sleeve 56 terminates in the region 60 and the trigger wires 42, 50 and 54 extend out distally of the termination of the sleeve 56. The access sheaths 28 and 30 with their respective dilator catheters 32 and 34 and indwelling guide wires 36 and 38 extend through the short catheter 14. The short catheter 14 terminates at 62 just proximal of the sheath manipulator 10. The sheath manipulator 10 can be withdrawn over the short catheter 14 with the hemostatic seal 12 engaging against the short catheter to withdraw the sheath 6 from the stent graft during deployment.

Figure 4:
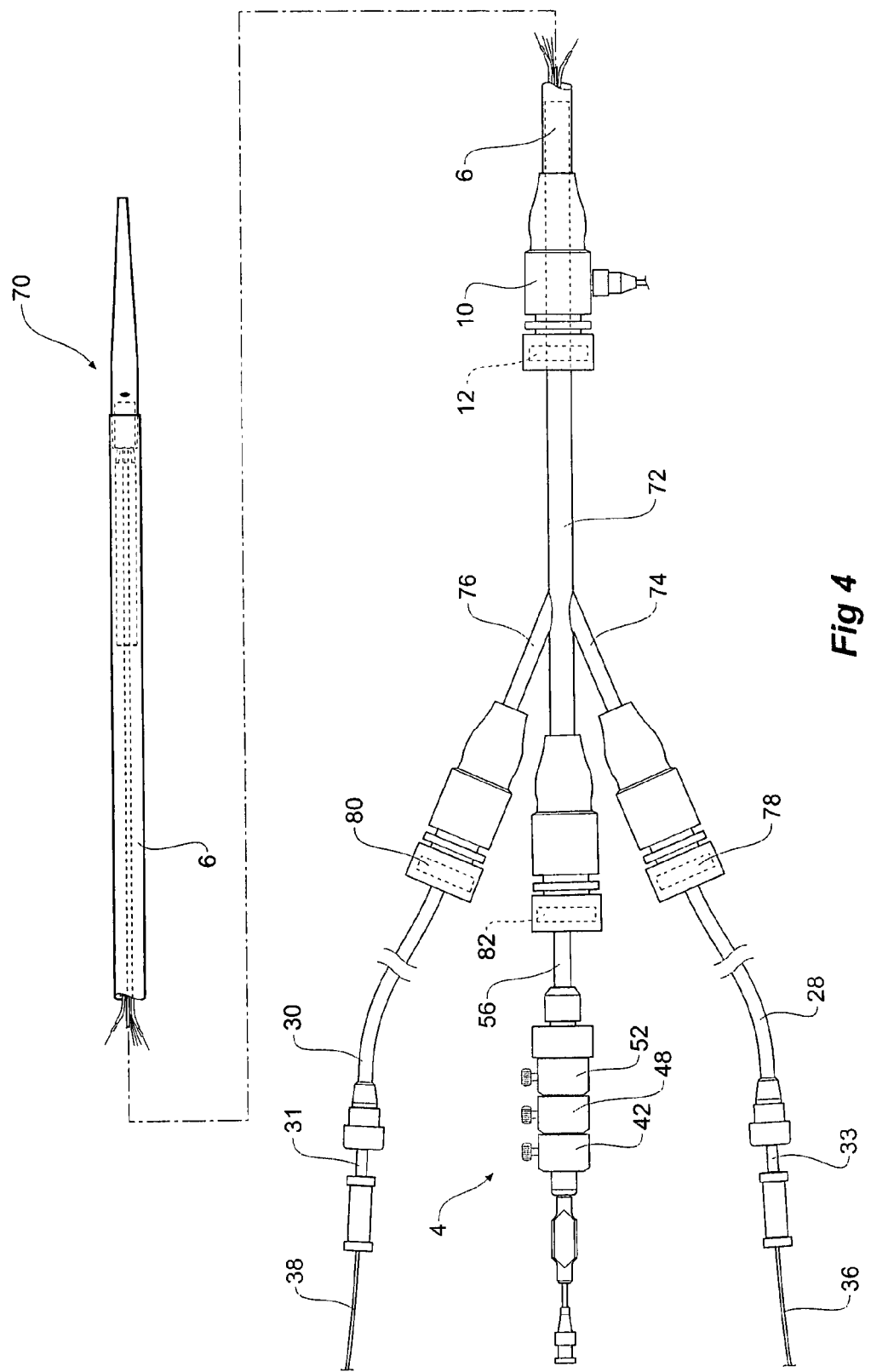
FIG. 4 shows an alternative embodiment of stent graft introducer according to the present invention.

FIG. 4 shows an alternative embodiment of stent graft introduction device according to the present invention. In this embodiment the proximal end of the introducer 70 is substantially the same as shown in FIGS. 1 and 2 and will not be discussed further.

In this embodiment, however, the short catheter 72 trifurcates into separate catheters 74 and 76. The leg 74 extends to a hemostatic seal 78 through which the access sheath 28 extends. The leg 76 extends to hemostatic seal 80 and through this the access sheath 30 extends. The sleeve 56 extends through hemostatic seal 82 to the handle assembly 4. The sheath manipulator 10 has a hemostatic seal 12 which seals against the short catheter 72 and enables manipulation of the sheath 6. On the handle assembly 4 are the trigger wire release mechanisms 42, 48 and 52.

Figure 5:
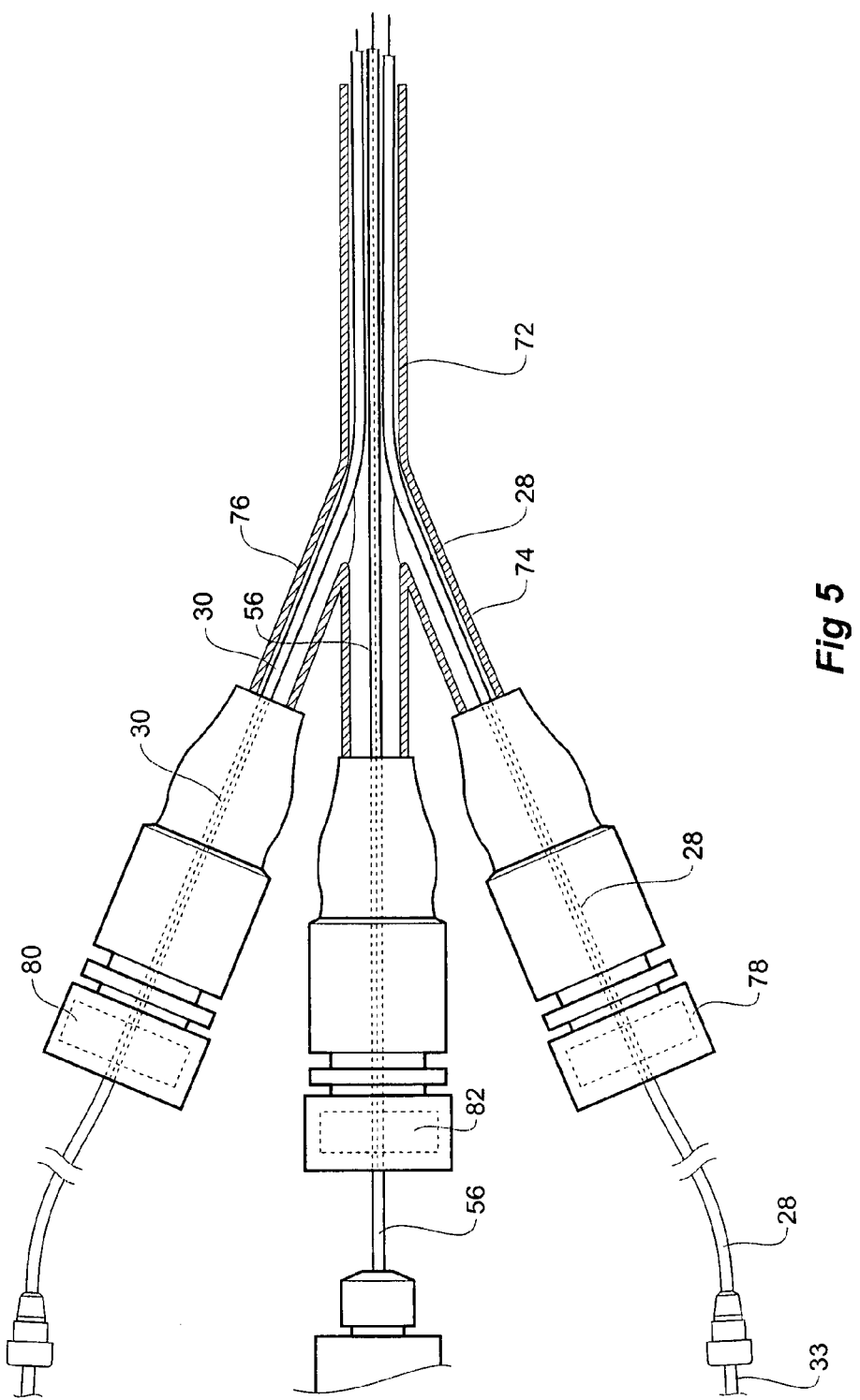
FIG. 5 shows a part cross-sectional view of detail of part of the introducer shown in FIG. 4.

FIG. 5 shows a cross-sectional view of part of the embodiment of FIG. 4 and in particular shows how the access sheath 28 and 30 and the guide wire catheter and sleeve 56 all pass through the short catheter 72. These are in fact shown in a plane view but in practice would distribute themselves in a substantially triangular manner in the short catheter 72 and in the sheath 6 (FIG. 4).

Figure 6:
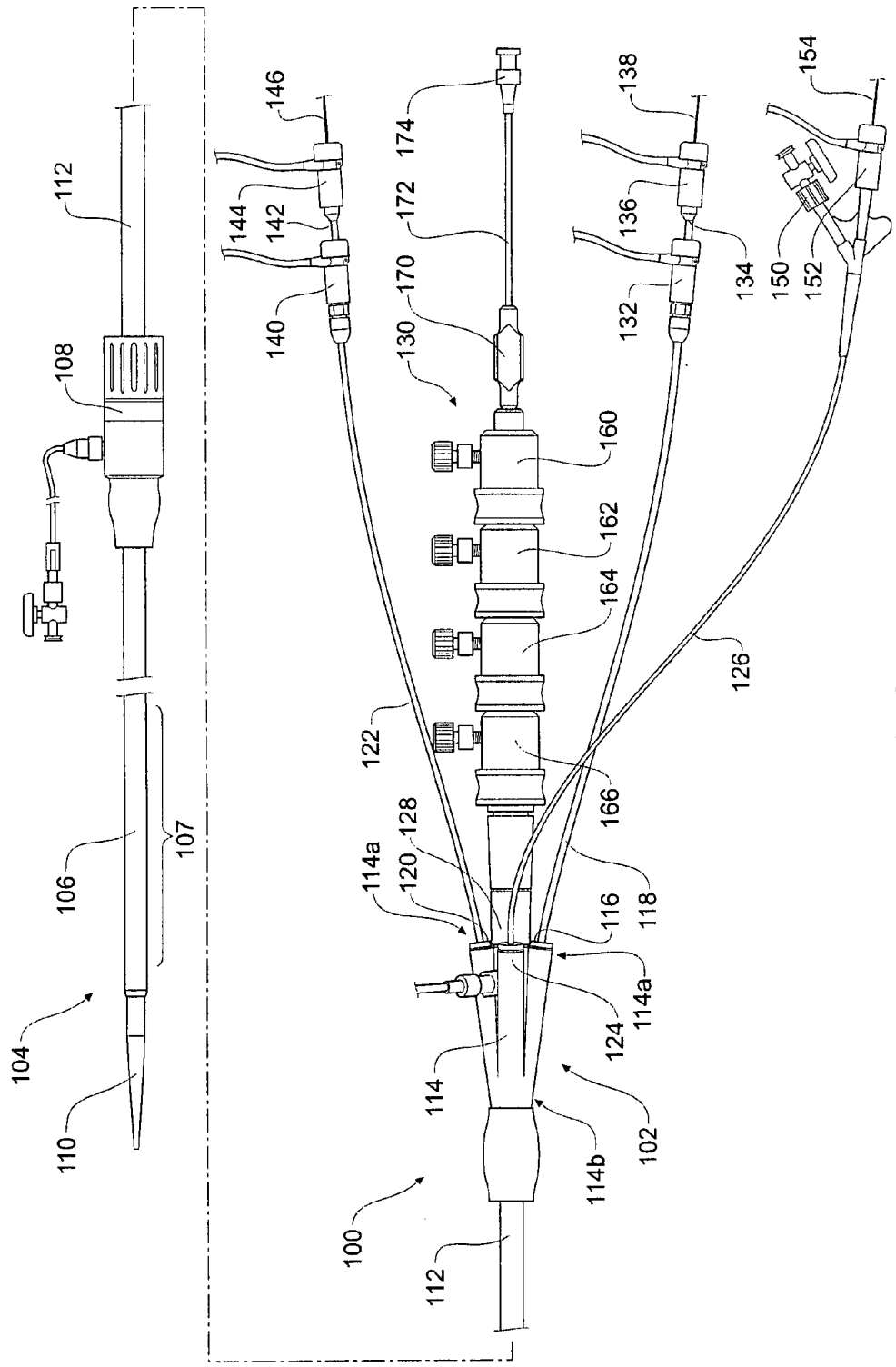
FIG. 6 shows an alternative embodiment of multi-port stent graft introducer incorporating a docking balloon arrangement according to the present invention.
Figure 7:
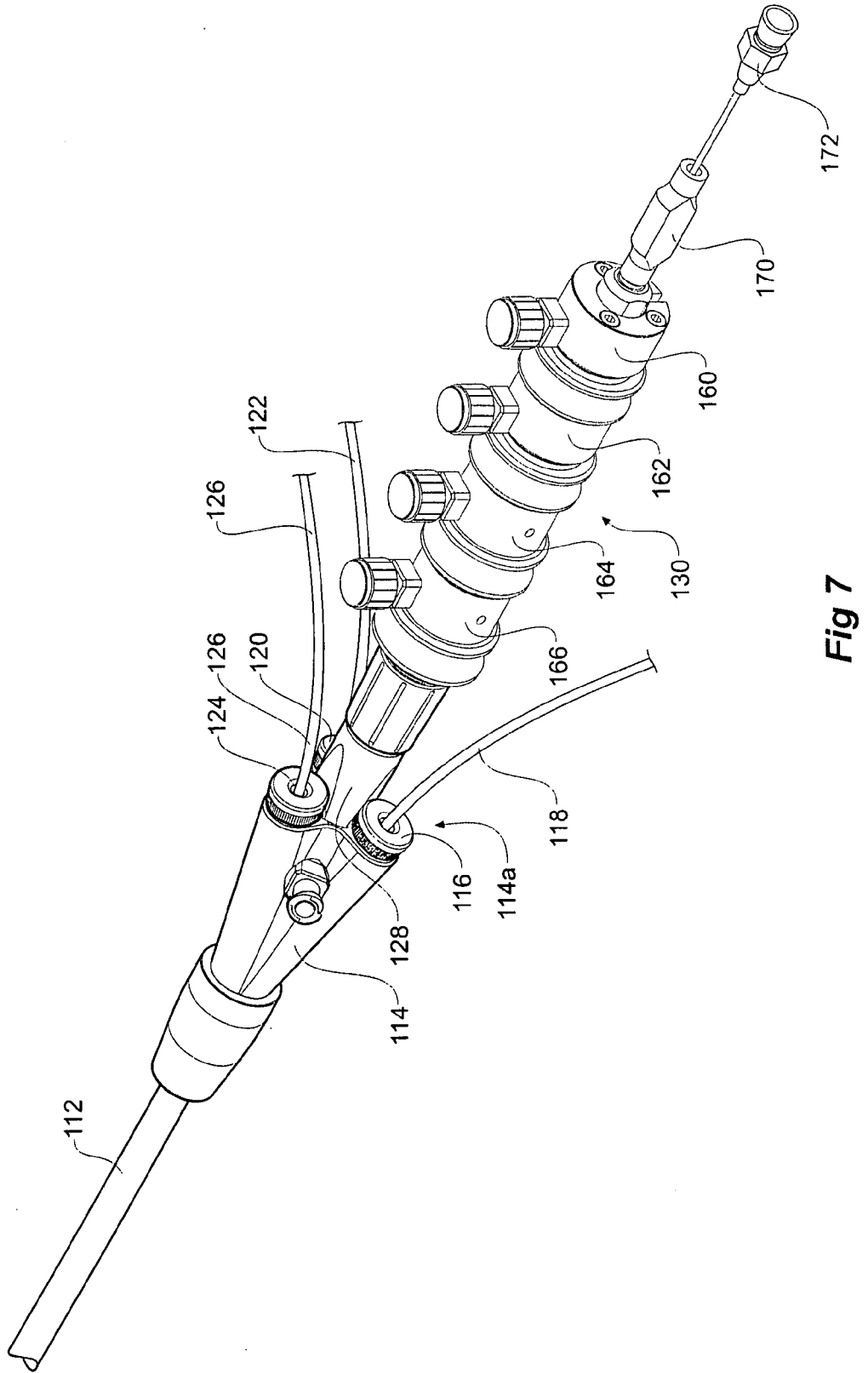
FIG. 7 shows detail of the handle portion of the multi-port stent graft introducer of FIG. 6.

FIG. 6 shows an alternative embodiment of multi port stent graft introducer incorporating a docking balloon arrangement according to the present invention. FIG. 7 shows in more detail the manifold and handle portion of the delivery device shown in FIG. 6.

The introducer device 100 shown in FIG. 6 comprises a handle and manifold assembly 102 and introduction portion 104 intended to be deployed into the patient. The introduction section 104 includes an outer sheath 106 extending from an outer sheath manipulator 108 to a nose cone dilator 110. A stent graft is retained within the outer sheath 106 in the region 107 just distal of the nose cone dilator 110 as is also schematically depicted in FIG. 2.

The outer sheath manipulator 108 is positioned over an inner sheath 112 which extends back and is fastened to the manifold 114. The inner sheath 112 extends proximal at least to a forward most position of the outer sheath manipulator 108 and preferably within the outer sheath to just distal of the stent graft retained within the outer sheath 106. The manifold 114 has a proximal end 114b to which is connected the outer sheath 112 and four access ports at its distal end 114a. Access port 116 is for a first access sheath 118. Access port 120 is for a second access sheath 122. A third access port 124 is for a docking balloon catheter 126.

A fourth port 128 provides access to the handle 130 which includes trigger wire release mechanisms as discussed below.

The access sheath 118 extends to a haemostatic seal 132 through which extends the dilator 134. On the dilator 134 is a dilator haemostatic seal 136 through which extends an indwelling guide wire 138.

The access sheath 122 extends to a haemostatic seal 140 through which extends the dilator 142. On the dilator 142 is a dilator haemostatic seal 144 through which extends an indwelling guide wire 146.

The balloon catheter 126 extends to an inflation port 150 and balloon catheter haemostatic seal 152. The auxiliary balloon guide wire 154 extends through the balloon catheter haemostatic seal 152.

The handle assembly 130 includes trigger wire release mechanisms as follows. Trigger wire release 162 is for the diameter reducing ties (see item 42 in FIG. 2), trigger wire release 160 is for the guide wire retention release wire (see item 92 in FIG. 2B). Trigger wire release 164 is for the retention trigger wire for the exposed stent in the capsule (see item 50 in FIG. 2). Trigger wire release mechanism 166 is for the distal end of the graft (see item 54 in FIG. 2).

A pin vice 170 is at the rear of the handle 130 and the guide wire catheter 172 for the introducer device extends through the pin vice 170 and is locked for movement with respect to the handle 130 by the pin vice. The guide wire catheter 172 terminates in a syringe point 174 to enable flushing liquid and radiopaque medium to be deployed through the delivery device.

FIGS. 8A to 8E show in a stylised manner the operation of a docking balloon arrangement for an alternative embodiment of the invention. Reference numerals are the same as those of FIG. 1 for corresponding items.

Figure 8:
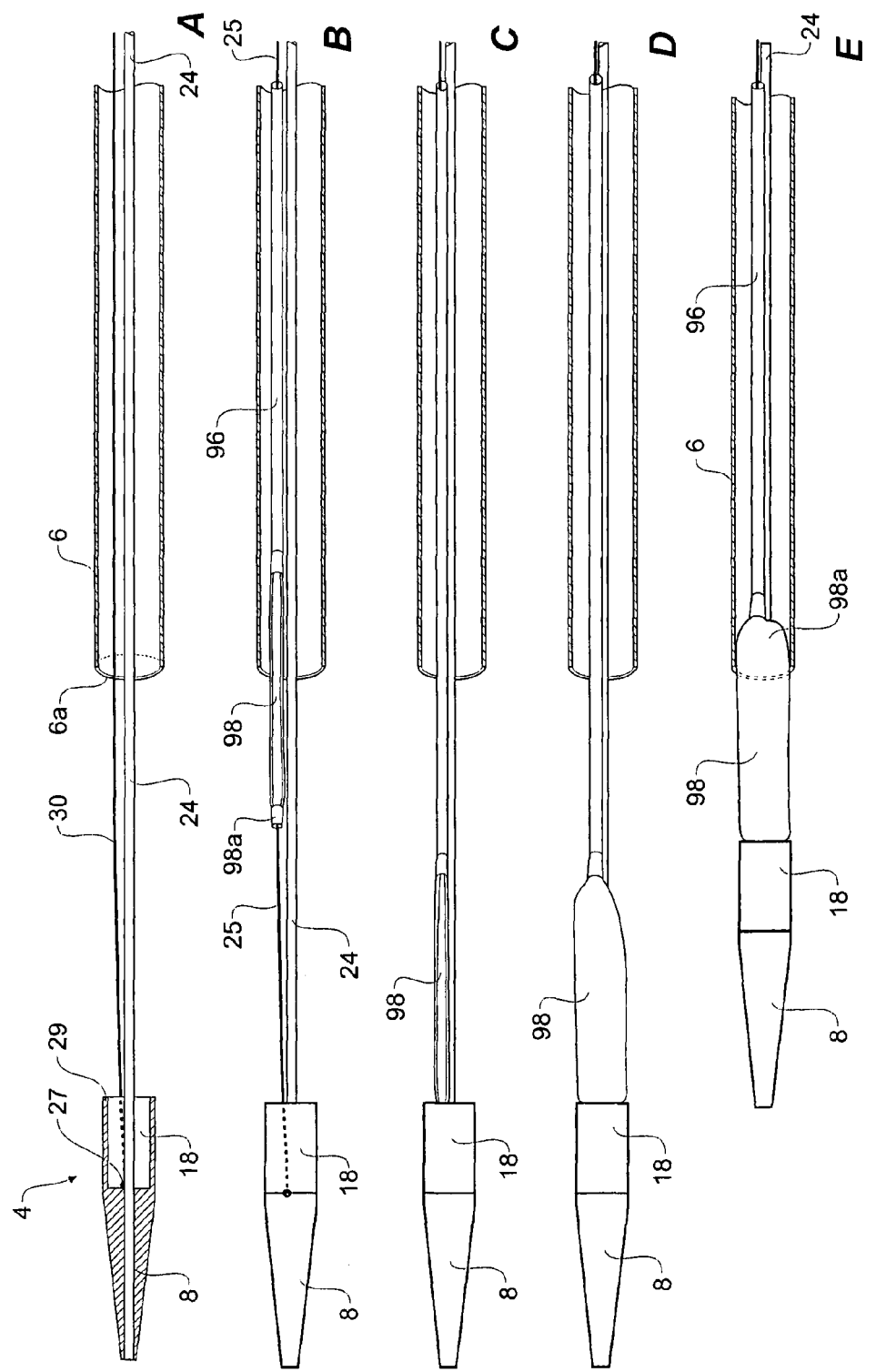
FIGS. 8A to 8E show in a stylised manner the operation of a docking balloon arrangement for an alternative embodiment of the invention.

In this embodiment as shown in FIG. 8A the stent graft introducer has a nose cone dilator 8 with a distally facing capsule 18 (shown in section in FIG. 8A) mounted onto a guide wire catheter 24. The guide wire catheter passes through the outer sheath 6. In this embodiment, however, there is an auxiliary guide wire 25 which extends substantially parallel to the guide wire catheter 24 and extends into the capsule 18 and is fixed inside the capsule and terminates at point 27. The auxiliary guide wire 25 extends through the sheath 6 and haemostatic seal 124 (see FIGS. 6 and 7) of the introducer.

After the stent graft has been deployed the introducer is as shown in FIG. 8A. At this stage, if the nose cone dilator 8 with capsule 18 is retracted to dock with the sheath 6 to enable their retraction together then the distal edge 29 of the capsule 18 could catch against portions of stents within an introduced stent graft and cause the stent graft to be dislodged. Similarly, if the sheath 6 is advanced so that the sheath docks with the capsule then the leading edge 6a of the sheath 6 could catch against portions of stents within an introduced stent graft and cause the stent graft to be dislodged. It is necessary to have some method of providing a fairing to prevent engagement with the stents of the stent graft.

As shown in FIG. 8B a balloon catheter 96 has been introducer over the auxiliary guide wire 25 through the hemostatic seal (not shown). The balloon catheter 96 includes a inflatable balloon 98.

The balloon catheter 96 and balloon 98 are advanced along the auxiliary guide wire 25 until its proximal end 98a is received within the capsule 18 as shown in FIG. 8C. The balloon 98 is then inflated as shown in FIG. 8D until it is substantially the same diameter as the capsule 18.

The nose cone 8, capsule 18 and balloon 98 can then be retracted by releasing the pin vice 49 (see FIG. 1) to allow movement of the guide wire catheter 24 with respect to the handle 4 (see FIG. 1) until the distal end of the balloon 98b is engaged within the sheath 6 as shown in FIG. 8E and then the introducer entire device 2 can be retracted without potential problems of engagement against stents of an already deployed stent graft. Alternatively the nose cone dilator 8, capsule 18, balloon 98 and guide wire catheter 24 can all be withdrawn leaving the sheath 6 in place.

A process for use of the delivery device of one embodiment of the invention is as follows.

In this embodiment the deployment device has the following components:
1). guide wire catheter
2). inner sheath
3). outer sheath
4). nose cone dilator with distally opening top capsule
5). indwelling guide wire through fenestration and into top cap
6). stabilisation retention of indwelling guide wire proximally of fenestration
7). access sheath on indwelling guide wire
8). auxiliary guide wire for docking balloon catheter
9). access sheath has a dilator within it extending to a dilator tip;
10). stent graft with
   i. proximally extending exposed stent
   ii. distal retention
   iii. fenestrations
   iv. radiopaque markers
   v. diameter reducing ties Introduction steps are as follows:
(a) Position the deployment device into the aorta correctly taking into account N-S position as well as rotational position with respect to target vessels and fenestrations on the stent graft using markers on stent graft body.
(b) Withdraw the outer sheath of the deployment device while continuing to check position until the distal end of the stent graft opens. At this stage the distal end of the stent graft is still retained by distal fixation, the proximal end is retained by the exposed stent retained in top capsule of the deployment device and the expansion of the stent graft is restricted by the diameter reducing ties.
(c) Advance the access sheaths (left and right) on their respective indwelling guide wires through lumen of stent graft to or through the fenestration (at this stage the top cap or capsule is still retaining the exposed stent and the indwelling guide wires).
(d) Position the access sheath at the opening of the fenestration or at the infundibulum of the hinged fenestration.
(e) Remove the dilator of the access sheath.
(f) Advance an additional catheter and additional guide wire (4-5 Fr) through the access sheath and into the target vessel. The additional catheter may have a crooked or hockey stick tip to facilitate access.
(g) Remove the guide wire from the additional catheter and re-insert a stiffer wire into the target vessel (eg renal artery).
(h) Release the stabilisation retention of indwelling guide wire
(i) Retrieve the indwelling wire guide from the top cap and pull it out completely.
(j) Remove the additional catheter and replace the access sheath dilator and dilator catheter over the stiffer wire in the target vessel and advance the access sheath over the stiffer wire into the target vessel. Withdraw the access sheath dilator.
(k) Repeat steps (d) to (j) for the other of the target vessels.
(l) Advance covered stents through the access sheaths into the target vessels but do not release.
(m) Release the diameter reducing ties.
(n) Release the top cap by removing the locking trigger wire and advancing the top cap on the guide wire catheter and release the top exposed stent.
(o) Release the distal attachment of the stent graft.
(p) One at a time, withdraw the access sheaths from the target vessels and deploy covered stents between the fenestrations and into the target vessels and balloon expand if necessary including flaring within the main stent graft.
(q) Remove both access sheaths and also the guide wires from the target vessels and withdraw them from the system.
(r) Advance a balloon catheter over the auxiliary guide wire until the proximal end of the balloon is in the top capsule.
(s) Inflate the balloon
(t) Retract the nose cone dilator, balloon catheter and auxiliary catheter to the outer sheath
(u) Withdraw the entire assembly or leave the outer sheath in place for further deployments. Further deployment may include a bifurcated distal component.

It is seen that by this invention an arrangement is provided that by which access sheaths may extend through the introduction device and are able to be separately manipulated to enable access to renal or other arteries within the vasculature of a patient.

What is claimed is:

1. A multi-port stent graft delivery device and stent graft in combination therewith, the delivery device comprising;
    a guide wire catheter having a guide wire lumen therethrough;
    a handle assembly at a distal end of the guide wire catheter, the handle including a plurality of access ports;
    a nose cone dilator at the proximal end of the guide wire catheter;
    a sheath arrangement extending from the handle to the nose cone dilator, the sheath arrangement being coaxial with and surrounding the guide wire catheter and defining an annular access lumen between the guide wire catheter and the sheath arrangement;
    the stent graft being on the guide wire catheter and within the main sheath, the stent graft comprising a proximal end, a distal end, a peripheral wall defining a lumen therethrough and at least one fenestration in the peripheral wall;
    the proximal end of the stent graft being releasably retained by a retention and release arrangement distally of the nose cone dilator;
    at least one indwelling access sheath within the access lumen, the at least one indwelling access sheath extending from the or one of the access ports and the indwelling access sheath having a proximal end terminating distally of the stent graft;
    a dilator extending through the or each access sheath and comprising a dilator tip at the proximal end of the or each access sheaths, the dilator being able to be withdrawn through the access sheath,
    an indwelling guide wire within the or each dilator in its access sheath;
    the indwelling guide wire extending beyond the dilator tip through the stent graft and then exiting the at least one fenestration and then extending proximally within the main sheath;
    whereby upon deployment of the stent graft into the vasculature of a patient the indwelling guide wire can be used to facilitate catheterization of a side branch or target vessel or be used to stabilize the access sheath during catheterization, advancement of the access sheath into the target vessel and deployment of a covered or uncovered stent therein through the access sheath.

2. A multi-port stent graft delivery device as in claim 1 wherein the retention and release arrangement distal of the nose cone dilator for the proximal end of the stent graft comprises a distally facing capsule fixed to the nose cone dilator and the proximal end of the stent graft is received on the capsule, the stent graft comprising a proximal exposed stent and the proximal exposed stent being received in the capsule and the stent graft being released by advancement of the nose cone dilator.

3. A multi-port stent graft delivery device as in claim 1 wherein the retention and release arrangement distal of the nose cone dilator for the proximal end of the stent graft comprises a trigger wire system engaging the stent graft or a stent of the stent graft, the stent graft comprising a proximal exposed stent and the proximal exposed stent being engaged by the trigger wire system.

4. A multi-port stent graft delivery device as in claim 1 wherein the stent graft includes diameter reducing ties thereby retaining the stent graft in a diameter reduced condition and the delivery device further includes a release arrangement on the handle for the diameter reducing ties.

5. A multi-port stent graft delivery device as in claim 1 wherein the release arrangement for the diameter reducing ties can comprise a first release grip on the handle and a release wire extending from the first release grip to the diameter reducing ties.

6. A multi-port stent graft delivery device as in claim 1 further including a retention arrangement for the distal end of the stent graft comprising a tie arrangement engaging a distal end of the stent graft, a second release grip on the handle and at least one trigger wire extending from the second release grip to the tie arrangement.

7. A multi-port stent graft delivery device as in claim 1 wherein the guide wire catheter comprises a sleeve to act as a guide for trigger wires.

8. A multi-port stent graft delivery device as in claim 1 wherein the sheath arrangement comprises an inner sheath extending proximally from the handle and a outer sheath including a sheath retractor on the inner sheath to withdraw the outer sheath to expose the stent graft.

9. A multi-port stent graft delivery device as in claim 1 wherein the handle assembly comprises a haemostatic seal assembly and the delivery catheter and the or each access sheath extends through the haemostatic seal assembly.

10. A multi-port stent graft delivery device as in claim 1 wherein the handle assembly comprises a bifurcated or trifurcated tube assembly comprising two or three arms extending from a main tube and a haemostatic seal and access port on each of the arms and a respective one of the delivery catheter and the or each indwelling access sheath extending through a respective tube and haemostatic seal and access port.

11. A multi-port stent graft delivery device as in claim 1 wherein the handle assembly comprises a manifold assembly having a manifold body with a single aperture an one end and three or four spaced apart access ports at another end and a haemostatic seal on each of the spaced access ports and a respective one of the delivery catheter and the or each indwelling access sheath extending through a respective access port and haemostatic seal.

12. A multi-port stent graft delivery device as in claim 1 wherein the fenestration or fenestrations in the stent graft can comprise a hinged fenestration, the hinged fenestration comprising an enlarged aperture in the peripheral wall of the stent graft and a smaller aperture within the enlarged aperture and a frusto-conical cone of graft material between the enlarged aperture and the smaller aperture.

13. A multi-port stent graft delivery device as in claim 1 wherein the indwelling guide wire extending through the stent graft and exiting the at least one fenestration and extending proximally within the main sheath is releasably fastened to the peripheral wall of the stent graft proximally of the fenestration to stabilise the indwelling guide wire during advancement of the dilator and access sheath and catheterisation of the branch vessel.

14. A multi-port stent graft delivery device as in claim 13 wherein the releasable fastening of the indwelling guide wire comprises in combination a release wire stitched into the peripheral wall of the stent graft proximally of the fenestration, an engagement protrusion on the indwelling guide wire and a suture engaged around the release wire and the indwelling guide wire distally of the engagement protrusion whereby upon retraction of the release wire the suture is released from engagement with the indwelling guide wire.

15. A stent graft delivery device and stent graft in combination therewith, the delivery device comprising;
- a guide wire catheter having a guide wire lumen therethrough;
- a handle assembly at a distal end of the guide wire catheter, the handle including a plurality of access ports;
- a nose cone dilator at the proximal end of the guide wire catheter, the nose cone dilator having a distally opening capsule thereon;
- a sheath arrangement comprising an inner sheath extending proximally from the handle and a outer sheath including a sheath retractor on the inner sheath and extending to the nose cone dilator to withdraw the outer sheath, the sheath arrangement being coaxial with and surrounding the guide wire catheter and defining an annular access lumen between the guide wire catheter and the sheath arrangement;
- the stent graft being on the guide wire catheter and within the main sheath, the stent graft having a peripheral wall defining a lumen therethrough and at least one fenestration in the peripheral wall;
- the stent graft having a proximally extending exposed stent and the exposed stent being releasably retained in the capsule of the nose cone dilator;
- at least one indwelling access sheath within the access lumen, the at least one indwelling access sheath extending from the or one of the access ports and the indwelling access sheath having a proximal end terminating distally of the stent graft;
- a dilator extending through the or each access sheath and comprising a dilator tip at the proximal end of the or each access sheaths, the dilator being able to be withdrawn through the access sheath,
- an indwelling guide wire within the or each dilator in its access sheath;
- the indwelling guide wire extending beyond the dilator tip through the stent graft and exiting the at least one fenestration and extending proximally within the main sheath and being received in the capsule of the nose cone dilator;
- whereby upon deployment of the stent graft into the vasculature of a patient the indwelling guide wire can be used to facilitate catheterization of a side branch or target vessel or be used to stabilize the access sheath during catheterization, advancement of the access sheath into the target vessel and deployment of a covered or uncovered stent therein through the access sheath.

16. A stent graft delivery device as in claim 15 further including a docking balloon arrangement comprising a balloon guide extending into the capsule and affixed therein whereby upon completion of deployment of the stent graft, a balloon catheter including an inflatable balloon thereon can be advanced over the balloon guide at least partially into the capsule whereby the balloon can be inflated therein to provide a smooth transition from the nose cone to a delivery catheter for retraction of the nose cone dilator through the deployed stent graft.

17. A multi-port stent graft delivery device and stent graft in combination therewith, the delivery device comprising;
- a guide wire catheter having a guide wire lumen therethrough;
- a handle at a distal end of the guide wire catheter, the handle comprising a manifold assembly having a manifold body with a single aperture at a proximal end and three spaced apart access ports at a distal end and a haemostatic seal on each of the spaced apart access ports;
- a nose cone dilator at the proximal end of the guide wire catheter, the nose cone dilator having a distally opening capsule thereon;
- a sheath arrangement comprising an inner sheath extending proximally from the handle and a outer sheath including a sheath retractor on the inner sheath and extending to the nose cone dilator to withdraw the outer sheath, the sheath arrangement being coaxial with and surrounding the guide wire catheter and defining an annular access lumen between the guide wire catheter and the sheath arrangement;
- the stent graft being on the guide wire catheter and within the main sheath, the stent graft having a peripheral wall defining a lumen therethrough and at least one fenestration in the peripheral wall;
- the stent graft having a proximally extending exposed stent and the exposed stent being releasably retained in the capsule of the nose cone dilator;
- two access sheaths within the access lumen, the access sheaths extending from one of the spaced apart access ports in the manifold assembly and through the access lumen proximally and having a proximal end terminating distally of the stent graft;
- a dilator and indwelling guide wire within the or each access sheath;
- the indwelling guide wire extending beyond the dilator and access sheath through the stent graft and exiting the fenestration and extending proximally within the main sheath and being received in the capsule of the nose cone dilator;
- a respective one of the delivery catheter and the or each indwelling access sheath extending through a respective access port and haemostatic seal;
- a docking balloon arrangement comprising a balloon guide extending from one of the spaced apart access ports in the manifold assembly and through the access lumen proximally into the capsule and affixed therein;
- whereby upon deployment of the stent graft into the vasculature of a patient the indwelling guide wire can be used to facilitate catheterization of a side branch or target vessel or be used to stabilize the access sheath during catheterization, advancement of the access sheath into the target vessel and deployment of a covered or uncovered stent therein through the access sheath.

18. A multi-port stent graft delivery device as in claim 17 wherein the balloon guide comprises a balloon catheter whereby upon completion of deployment of the stent graft, the balloon catheter including an inflatable balloon thereon can be advanced through the access port over the balloon guide at least partially into the capsule whereby the balloon can be inflated therein to provide a smooth transition from the nose cone to a delivery catheter for retraction of the nose cone dilator through the deployed stent graft.

19. A multi-port stent graft delivery device as in claim 17 wherein the balloon catheter is resident in the deployment device and the balloon catheter is advanced into the capsule upon completion of deployment of the stent graft.

20. A multi-port stent graft delivery device as in claim 19 wherein the releasable fastening of the indwelling guide wire comprises in combination a release wire stitched into the peripheral wall of the stent graft proximally of the fenestration, an engagement protrusion on the indwelling guide wire and a suture engaged around the release wire and the indwelling guide wire distally of the engagement protrusion whereby upon retraction of the release wire the suture is released from engagement with the indwelling guide wire.

21. A multi-port stent graft delivery device as in claim 17 wherein the indwelling guide wire extending through the stent graft and exiting the at least one fenestration and extending proximally within the main sheath is releasably fastened to the peripheral wall of the stent graft proximally of the fenestration to stabilize the indwelling guide wire during advancement of the dilator and access sheath and catheterization of the branch vessel.

* * * * *